United States Patent
Utani et al.

(10) Patent No.: US 8,020,458 B2
(45) Date of Patent: Sep. 20, 2011

(54) SAMPLE INTRODUCING SYSTEM

(75) Inventors: Keisuke Utani, Kako-gun (JP); Kohei Nishiguchi, Kako-gun (JP)

(73) Assignee: Sumitomo Seika Chemicals Co., Ltd, Hyogo (JP)

( * ) Notice: Subject to any disclaimer, the term of this patent is extended or adjusted under 35 U.S.C. 154(b) by 545 days.

(21) Appl. No.: 12/227,075

(22) PCT Filed: Mar. 30, 2007

(86) PCT No.: PCT/JP2007/057160
§ 371 (c)(1),
(2), (4) Date: Nov. 6, 2008

(87) PCT Pub. No.: WO2007/129513
PCT Pub. Date: Nov. 15, 2007

(65) Prior Publication Data
US 2009/0173171 A1    Jul. 9, 2009

(30) Foreign Application Priority Data
May 9, 2006   (JP) .................................. 2006-130626

(51) Int. Cl.
*G01N 1/22* (2006.01)
(52) U.S. Cl. .................................................. 73/863.23
(58) Field of Classification Search ........................ None
See application file for complete search history.

(56) References Cited

U.S. PATENT DOCUMENTS

| | | | |
|---|---|---|---|
| 5,259,254 A | 11/1993 | Zhu et al. | |
| 5,400,665 A | 3/1995 | Zhu et al. | |
| 5,477,048 A | 12/1995 | Nakagawa et al. | |
| 6,021,678 A | 2/2000 | Vardiman et al. | |
| 2005/0258360 A1 | 11/2005 | Whitehouse et al. | |

FOREIGN PATENT DOCUMENTS

| | | |
|---|---|---|
| JP | 52-045267 | 10/1977 |
| JP | 05-002846 | 1/1993 |
| JP | 05-172750 | 7/1993 |
| JP | 2001-239181 | 9/2001 |
| WO | WO-90/09585 | 8/1990 |

OTHER PUBLICATIONS

Aug. 18, 2004, "Kitai Shiryo Chokusetsu Donyu Sochi no Shisaku to Seino Hyoka", Kohei Nishiguchi et al., The Japan Society for Analytical Chemistry Dai 53 Nenkai Koen Yoshishu , p. 9.

Jan. 1998, Reduction of water loading effects in inductively coupled plasma mass spectrometry by a Nafion membrane dryer device, Neil Fitzgerald, et al., Journal of Analytical Atomic Spectrometry, vol. 13, pp. 13-16.

*Primary Examiner* — Robert R Raevis
(74) *Attorney, Agent, or Firm* — Jordan and Hamburg LLP

(57) ABSTRACT

In a sample introducing system that can be easily adapted to a variety of analytical conditions without being affected by a flow rate of gas introduced into an analytical device, can introduce an analytical sample into the analytical device without loss, and can contribute to a simple and highly accurate high-sensitivity analysis, a pretreatment device removes unnecessary components from an untreated sample gas containing the analytical sample. A treated sample gas that has been pretreated by the pretreatment device is introduced into the analytical device via a connection gas flow channel. A gas addition device that adds a carrier gas to the treated sample gas flowing toward the analytical device in the connection gas flow channel has a means for changing the addition flow rate of the carrier gas. Pressure fluctuations of the gas containing the analytical sample are restricted by a pressure adjusting device upstream of the gas addition device.

8 Claims, 11 Drawing Sheets

[Fig. 1]
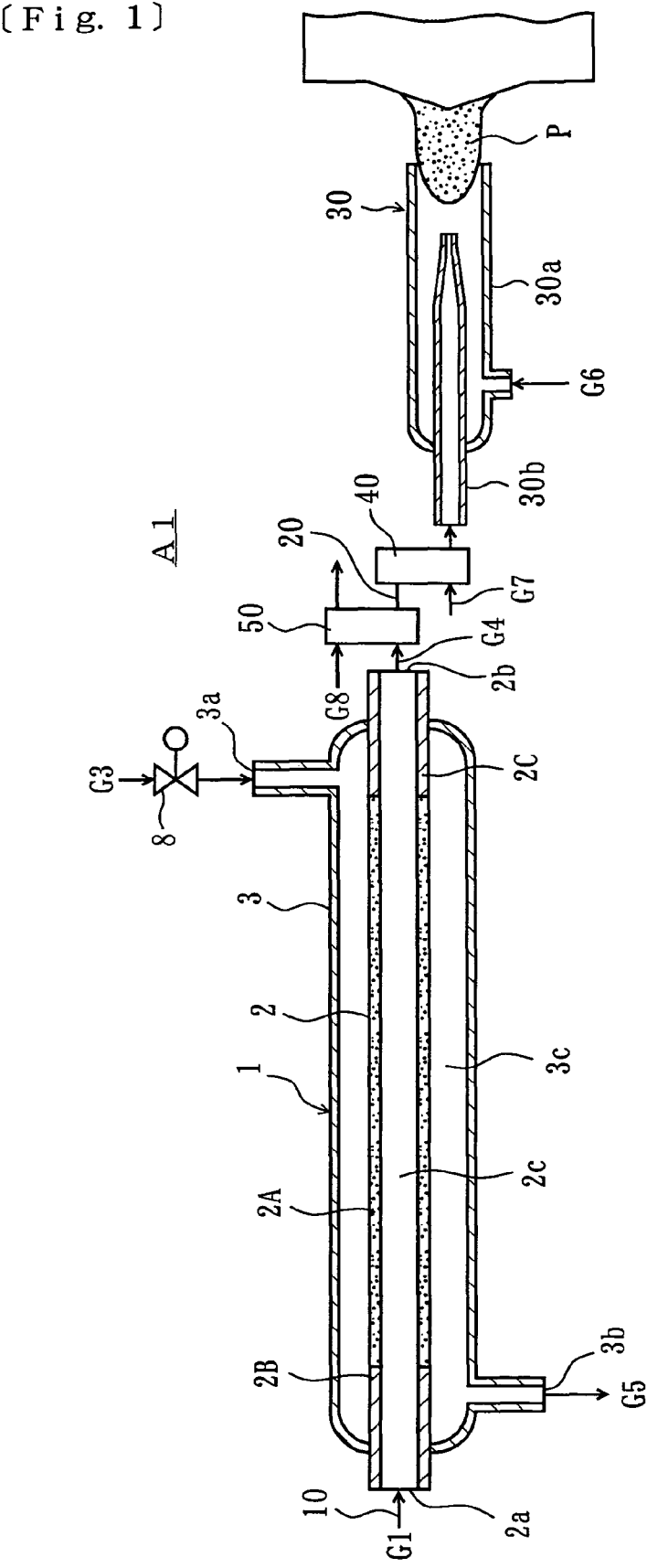

[Fig. 2]
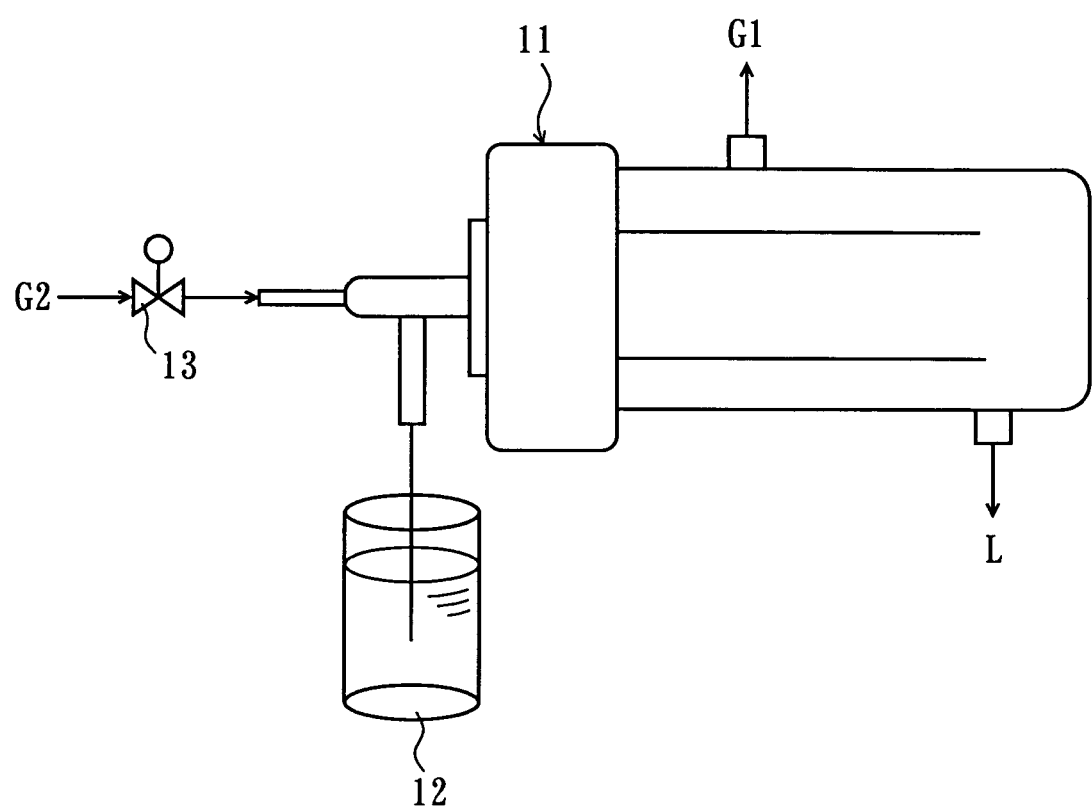

[Fig. 3]
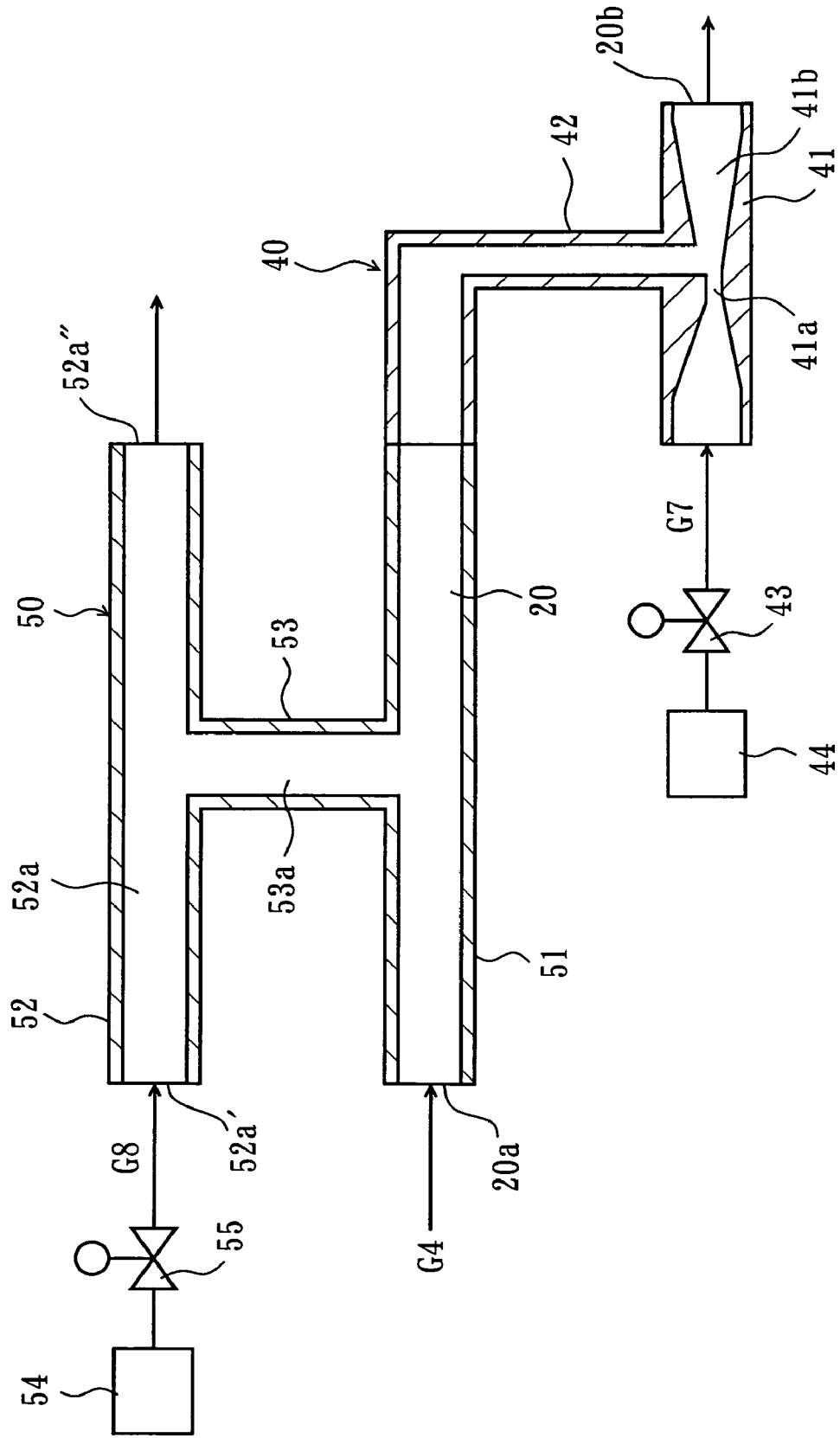

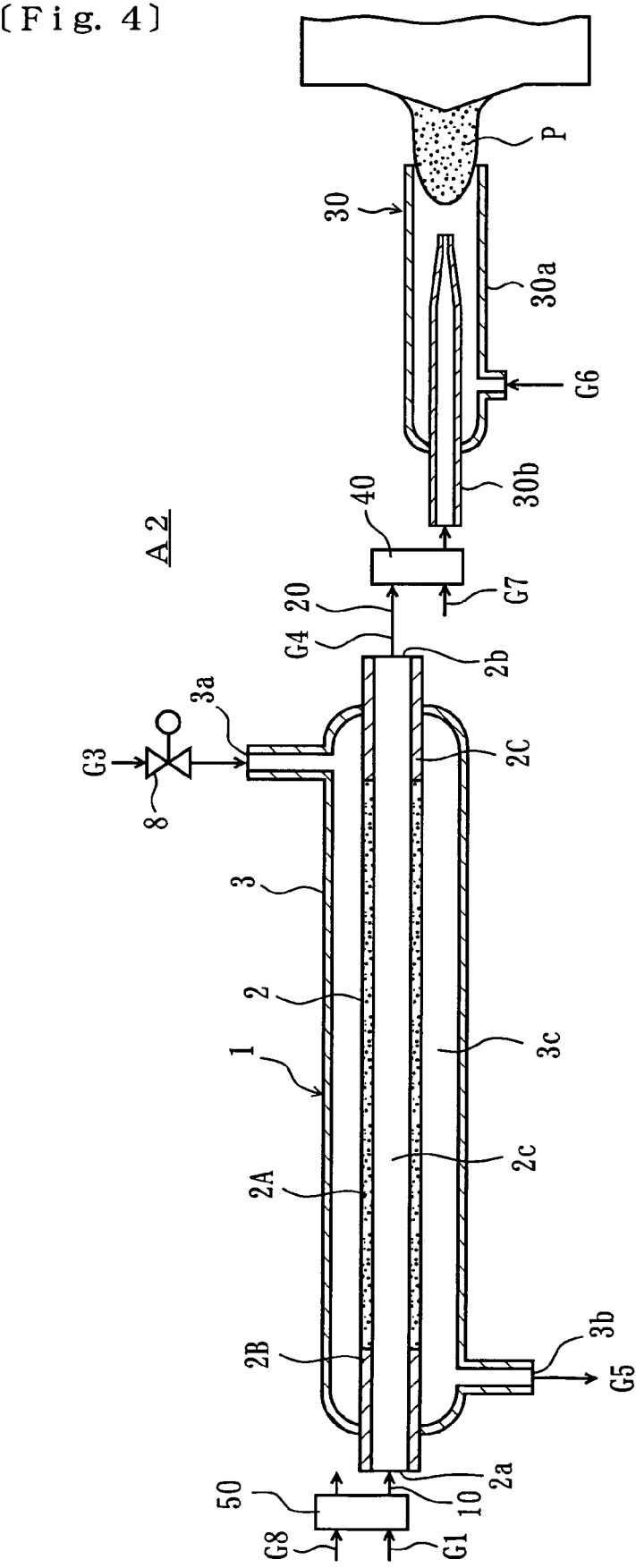
[Fig. 4]

[Fig. 5]
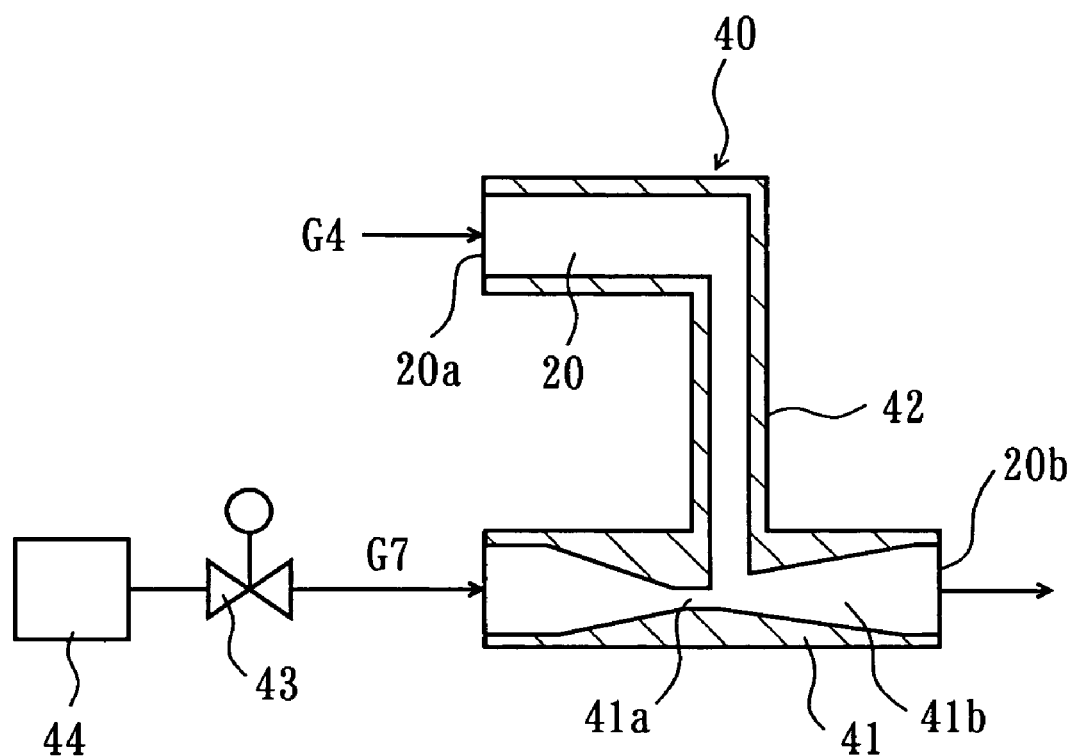

[Fig. 6]
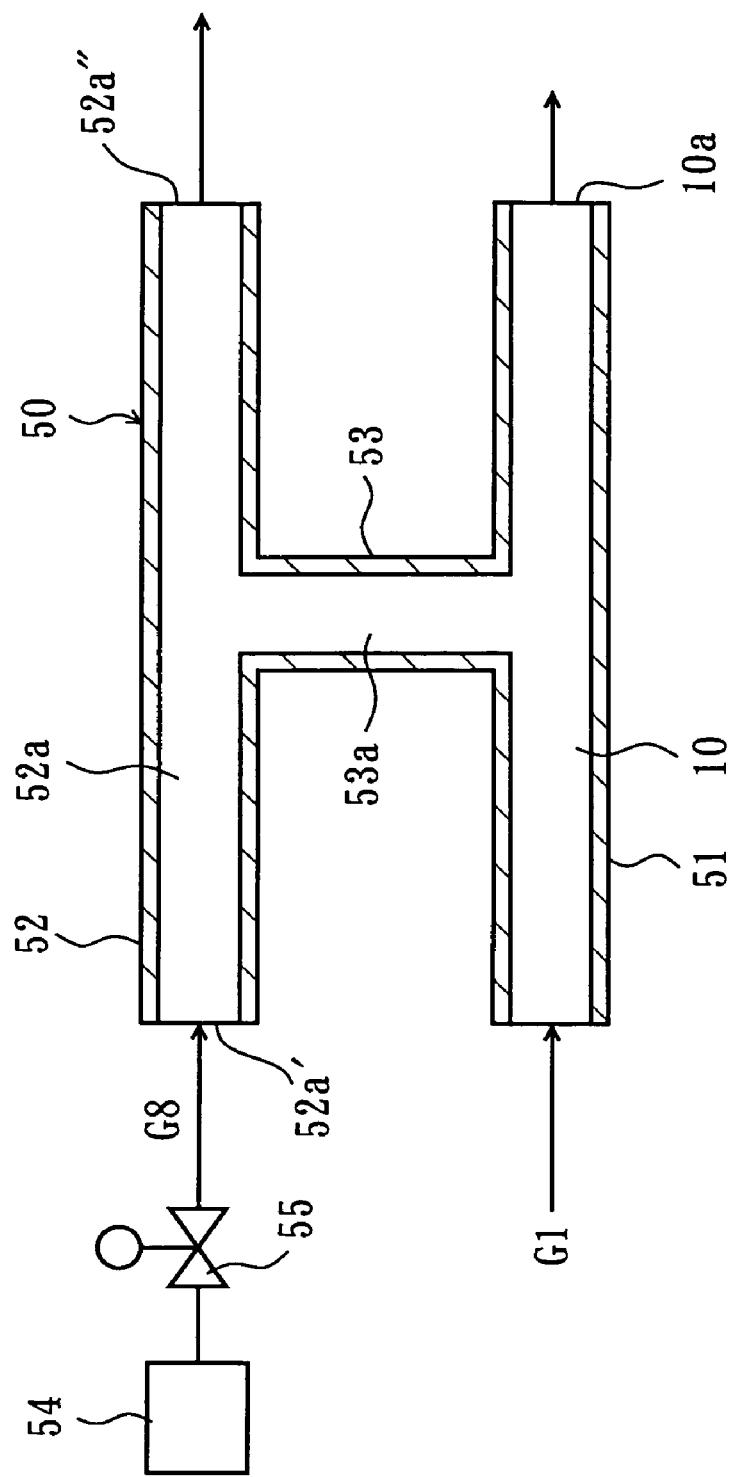

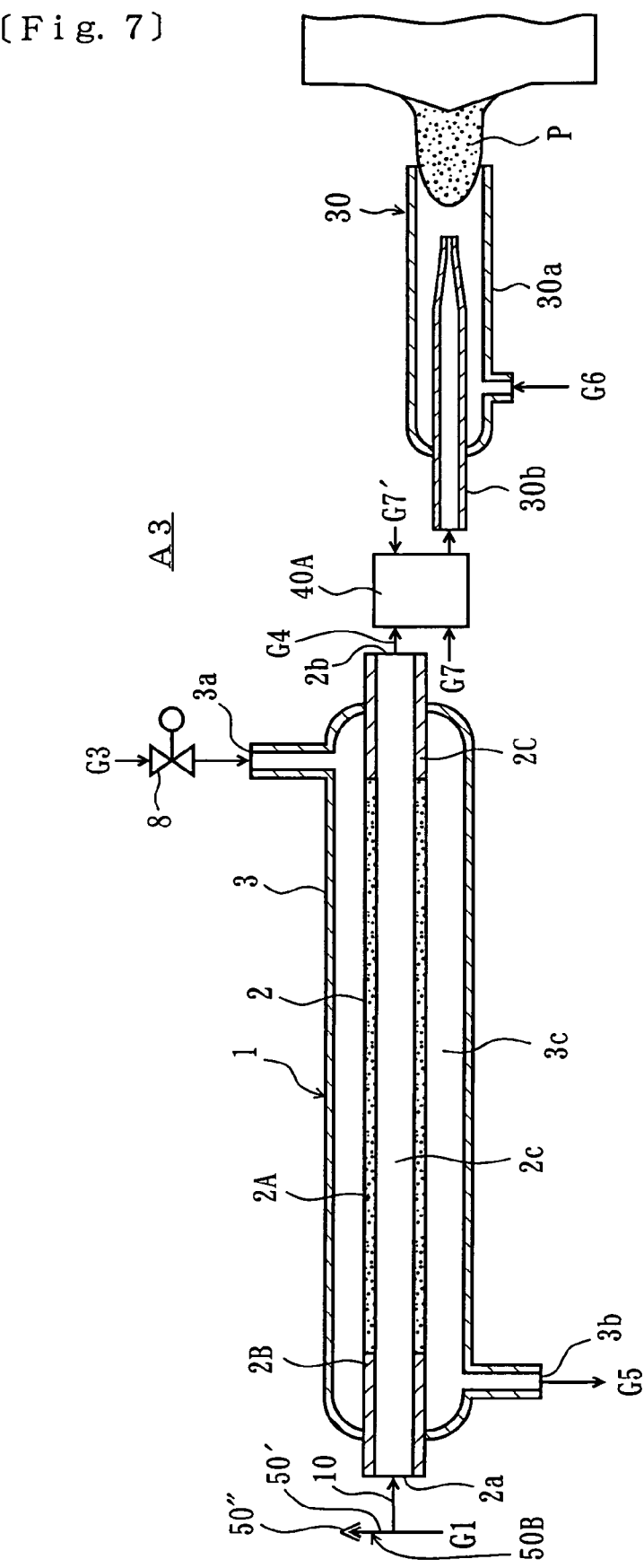
[Fig. 7]

[Fig. 8]
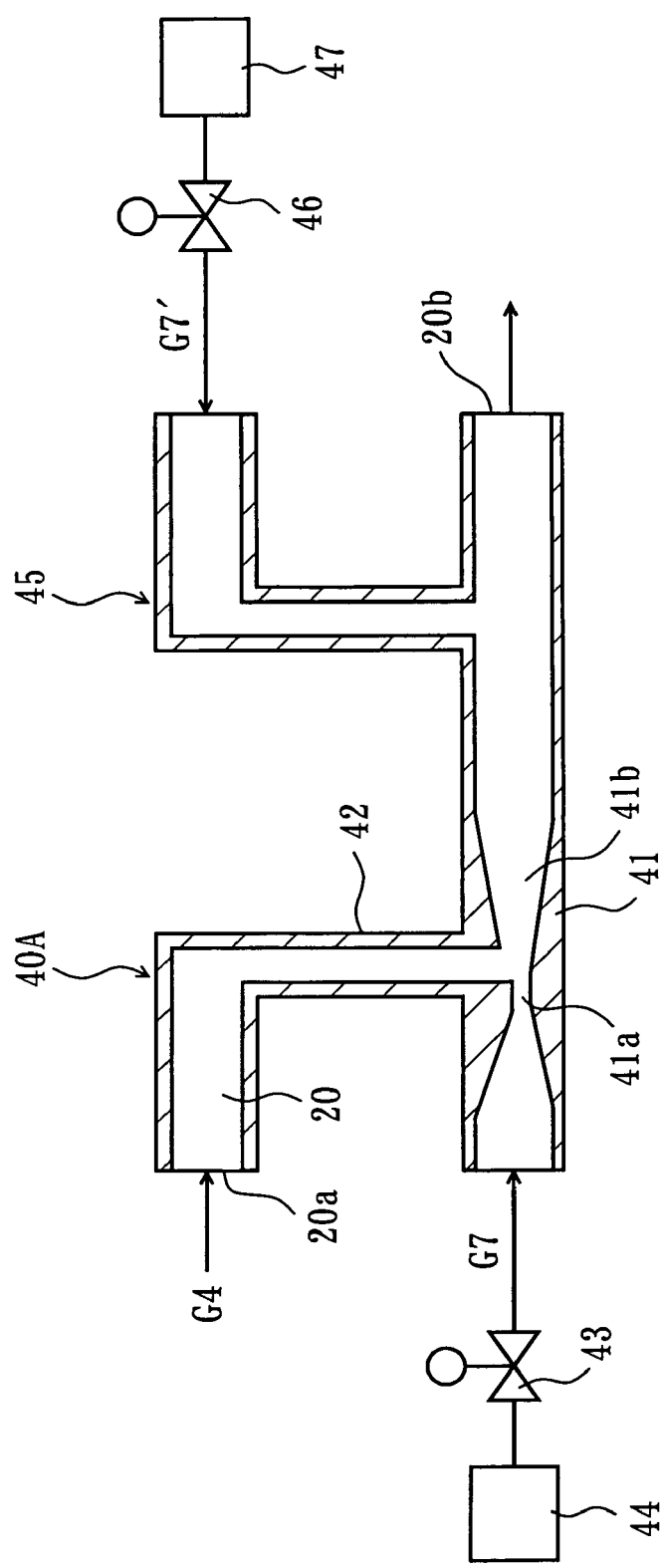

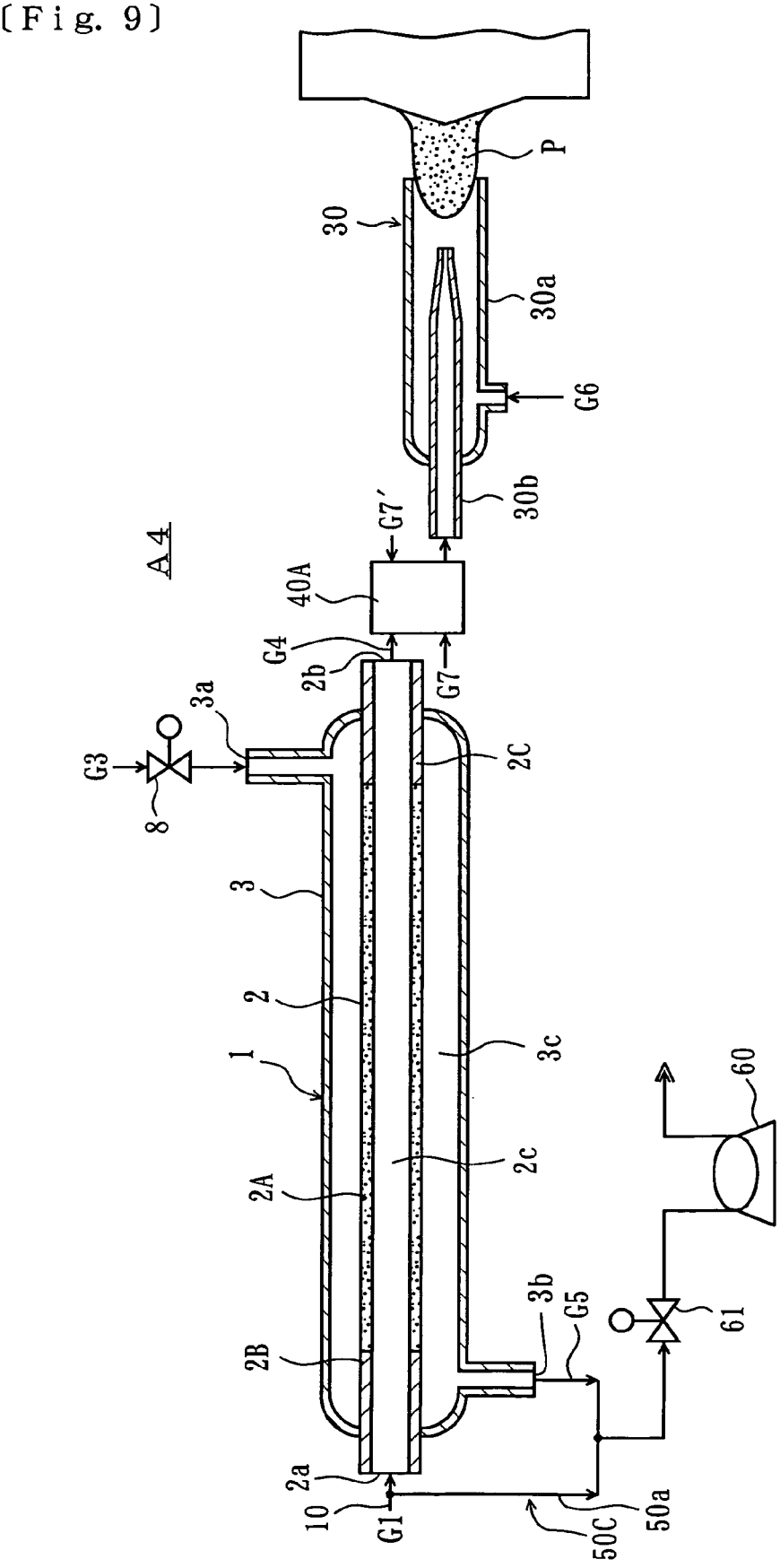
[Fig. 9]

[Fig. 10]
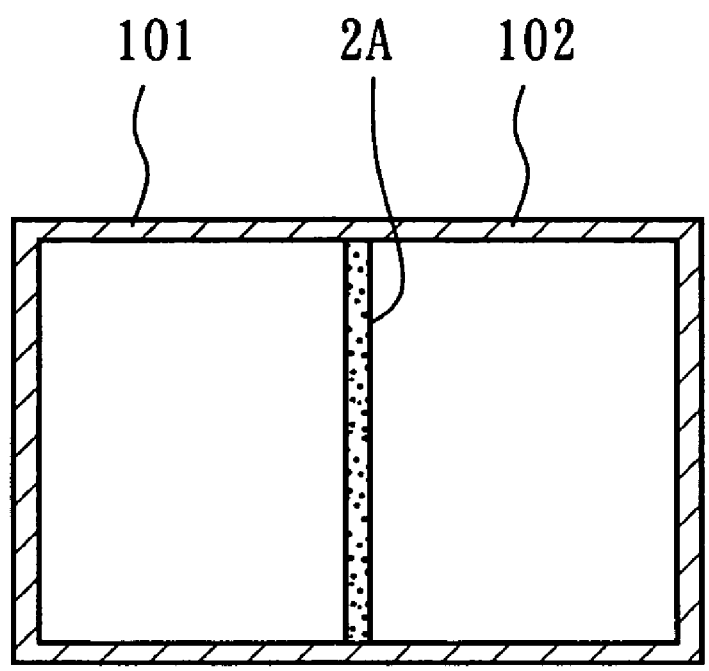

[Fig. 11]
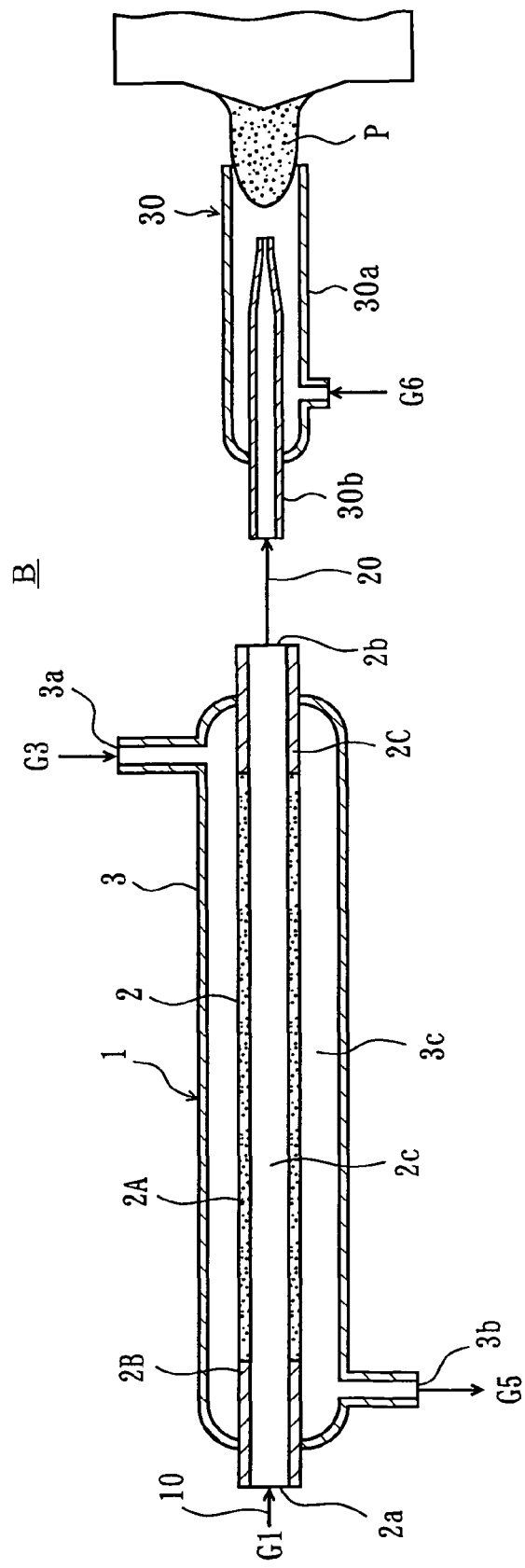

SAMPLE INTRODUCING SYSTEM

TECHNICAL FIELD

The present invention relates to a sample introducing system for introducing an analytical sample into an analytical device.

BACKGROUND

In recent years, concern about quality of living and working environment is risen, so that advanced analytical methods for measuring the composition and concentration of fine particles present in the atmosphere are sought. Further, in industries such as a semiconductor industry in which increased purity of material gases and atmosphere gas control in the manufacturing process are required, it is required to perform highly accurate analysis of the material gases containing fine particles and atmosphere gases in a simple manner.

Accordingly, analysis of analytical samples such as fine particles contained in a sample gas and specific gas components has been performed with analytical devices using highly sensitive analytical methods such as a gas chromatography spectrometry (GC-MS), an inductively coupled plasma analysis method (ICP method), and a microwave induced plasma analysis method (MIP method). For example, in the ICP method and MIP method, the analysis is performed by generating high-temperature plasma by using argon gas, nitrogen gas, helium gas and the like as a plasma gas, introducing an analytical sample into the plasma, and detecting signal variations from the plasma.

In order to analyze accurately the analytical sample contained in such sample gas, a pretreatment device is necessary that performs the pretreatment of removing unnecessary components from the sample gas. For example, when a sample gas containing a gaseous analytical sample is used, moisture, impurity gas components and the like other than the analytical sample contained in the sample gas are required to be removed as unnecessary components. Further, when a solution in which an analytical sample is dissolved in a solvent is converted into droplets floating in a spraying gas with a sprayer or the like and the spraying gas is used as the sample gas, it is required to remove moisture, solvent vapor and the like contained in the sample gas as unnecessary components.

A gas replacement device, a fine particle classification device, a drier or the like is used as the pretreatment device. For example, in the gas pretreatment device described in Patent Document 1, a sample gas is generated by converting a solvent having an analytical sample dissolved therein into a mist with a sprayer, the sample gas is heated to separate droplets into solvent vapor and an analytical sample, the sample gas is introduced in a tubular sealed filter made from a porous material, and the solvent vapor is removed by diffusion to the outside of the sealed filter. In the fine particle classification device described in Patent Document 2, in the process of electrically charging and classifying fine particles that are an analytical sample contained in the sample gas, gaseous contaminating components contained in the sample gas are removed and the fine particles are suspended in an atmosphere composed of a desired gas species. In the drier described in Non-patent Document 1, a sample gas is generated by converting an aqueous solution having an analytical sample into a mist, and moisture contained in the sample gas is removed via a non-porous membrane made of Nafion (trade name of Du Pont Co.; copolymer of perfluoro-3,6-dioxa-4-methyl-7-octene-sulfonic and tetrafluoroethylene).

A flow rate of gas containing an analytical sample introduced into an analytical device is changed correspondingly to the type or the like of elements constituting the analytical sample, in order to satisfy the optimum analytical conditions. For example, in a high-sensitivity analysis using plasma, in order to analyze a plurality of elements that are the objects of analysis and contained in the analytical sample, automatic tuning is performed to switch automatically the flow rate of gas introduced together with the analytical sample into the plasma. Further, in the mass analysis using the ionization action of plasma, the flow rate of gas introduced into plasma is automatically changed so as to prevent polyatomic ions having a mass number equal to that of the element that is an object of analysis from hindering the analysis.

Patent Document 1: Published Japanese Translation of a PCT Application No. H7-500416.
Patent Document 2: Japanese Patent Application Laid-open No. 2001-239181.
Non-patent Document 1: Journal of Analytical Atomic Spectrometry, January 1998, vol. 13 (13-18).

DISCLOSURE OF THE INVENTION

Problem to be Solved by the Invention

A flow rate of an untreated sample gas introduced into the pretreatment device has been conventionally changed in order to change the flow rate of gas introduced together with an analytical sample into an analytical device. However, when the flow rate of the untreated gas introduced into the pretreatment device is changed, the flow rate or pressure of the sample gas in the pretreatment device also changes; therefore, treatment conditions have to be changed according to this change. As a result, it is difficult to adapt to a variety of analytical conditions, and the sample cannot be introduced in a simple manner. Further, pressure fluctuations of gas occur in a gas flow channel between the pretreatment device and analytical device, and there is a risk that the seal is ruptured and contaminating substances contained in the ambient atmosphere penetrate into the analytical device. In particular, in a plasma analytical device, temperature variations or electron density variations are induced in plasma, stable plasma cannot be maintained, and there is a risk that high-sensitivity analysis is impeded.

DISCLOSURE OF THE INVENTION

The sample introducing system in accordance with the present invention includes a pretreatment device that performs a pretreatment of removing unnecessary components from an untreated sample including an analytical sample; a connection gas flow channel that introduces a treated sample gas treated by the pretreatment device into an analytical device; a gas addition device that adds a carrier gas to the treated sample gas that flows toward the analytical device in the connection gas flow channel; and a pressure adjusting device that restricts pressure fluctuations of a gas including the analytical sample upstream of the gas addition device, wherein the gas addition device includes changing means for changing an addition flow rate of the carrier gas.

In accordance with the present invention, the addition flow rate of the carrier gas to the treated sample gas flowing in the connection gas flow channel between the pretreatment device and the analytical device is changed by the gas addition device, and pressure fluctuations of the gas including the analytical sample are restricted by the pressure adjusting device upstream of the gas addition device. As a result, the flow rate of the gas introduced into the analytical device together with the analytical sample can be changed without changing the flow rate of the untreated sample gas introduced into the pretreatment device and without causing pressure fluctuations of the gas including the analytical sample in the pretreatment device. As a consequence, it is not necessary to change the conditions of treatment performed by the pretreatment device; therefore, it is possible to adapt to a variety of analytical conditions. Furthermore, because pressure fluctuations of the gas including the analytical sample are restricted upstream of the gas addition device, contaminating substances in the ambient environment or the like can be prevented from penetrating the analytical device via a seal or the like into the connection portion of the pretreatment device and the connection gas flow channel, and the treated sample gas can be prevented from leaking to the outside. Therefore, stable analytical results can be obtained, particularly in a plasma analytical device, stable plasma can be maintained without causing temperature variations or electron density variations in the plasma, thereby enabling high-sensitivity analysis.

It is preferable that the pressure adjusting device has a seal gas flow channel and a communication flow channel; the seal gas flow channel has an inlet port connected to a supply source of a seal gas and an outlet port communicating with an ambient atmosphere or an atmosphere under a constant pressure; a zone between the inlet port and the outlet port of the seal gas flow channel communicates via the communication flow channel with a zone between the gas addition device and the pretreatment device in the connection gas flow channel; setting means for setting an introduction flow rate of the untreated sample gas to the pretreatment device is provided; and the introduction flow rate of the untreated sample gas is set to a constant value.

As a result, the zone between the gas addition device and the pretreatment device in the connection gas flow channel communicates with the ambient atmosphere or an atmosphere under a constant pressure, and the introduction flow rate of the untreated sample gas to the pretreatment device becomes constant. Therefore, when the addition flow rate of the carrier gas is changed, pressure fluctuations of gas in the pretreatment device can be reliably prevented, without changing the flow rate of the untreated sample gas introduced in the pretreatment device. Further, sealing between the sample introducing system and the outside can be ensured with the seal gas flowing in the seal gas flow channel. Thus, pressure fluctuations of gas in the pretreatment device can be restricted and the pretreatment device can be sealed from the ambient environment, without using movable components.

Further, the sample introducing system in accordance with the present invention preferably includes an introducing flow channel for introducing the untreated sample gas into the pretreatment device; wherein the pressure adjusting device has a seal gas flow channel and a communication flow channel; the seal gas flow channel has an inlet port connected to a supply source of a seal gas and an outlet port communicating with an ambient atmosphere or an atmosphere under a constant pressure; a zone between the inlet port and the outlet port of the seal gas flow channel communicates via the communication flow channel with the introducing flow channel; setting means for setting an introduction flow rate of the untreated sample gas to the pretreatment device is provided; and the introduction flow rate of the untreated sample gas is set to a constant value.

As a result, the introducing flow channel communicates with the ambient atmosphere or an atmosphere under a constant pressure, and the introduction flow rate of the untreated sample gas to the pretreatment device becomes constant. Therefore, when the addition flow rate of the carrier gas is changed, pressure fluctuations of gas in the pretreatment device can be reliably prevented without changing the flow rate of the untreated sample gas introduced in the pretreatment device. Further, sealing between the sample introducing system and the outside can be ensured with the seal gas flowing in the seal gas flow channel. Thus, pressure fluctuations of gas in the pretreatment device can be restricted and the pretreatment device can be sealed from the ambient environment, without using movable components.

The sample introducing system in accordance with the present invention also preferably includes an introducing flow channel for introducing the untreated sample gas into the pretreatment device; wherein the pressure adjusting device has a discharge flow channel that branches off from the introducing flow channel; the discharge flow channel has an outlet port communicating with an ambient atmosphere or an atmosphere under a constant pressure; setting means for setting a supply flow rate of the untreated sample gas to the introducing flow channel, and setting means for setting an introduction flow rate of the untreated sample gas to the pretreatment device are provided; the introduction flow rate of the untreated sample gas is set to a constant value; and a set value of the supply flow rate of the untreated sample gas is larger than a set value of the introduction flow rate.

As a result, the outlet port of the discharge flow channel communicates with the ambient atmosphere or an atmosphere under a constant pressure, and the introduction flow rate of the untreated sample gas to the pretreatment device becomes constant; therefore, pressure fluctuations of gas in the pretreatment device can be reliably prevented without changing the flow rate of the untreated sample gas introduced in the pretreatment device. Further, because the set value of the supply flow rate of the untreated sample gas to the introducing flow channel is larger than the set value of the introduction flow rate of the untreated sample gas to the pretreatment device, sealing between the sample introducing system and the outside can be ensured with the untreated sample gas flowing in the discharge flow channel. Thus, pressure fluctuations of gas in the pretreatment device can be restricted and the pretreatment device can be sealed from the ambient environment, without using movable components.

It is preferable that the analytical sample is in the form of solid fine particles; the pretreatment device has a porous partition; and a gas replacement function is realized with the pretreatment device by which at least part of gas components of the untreated sample gas are replaced with the replacement gas via diffusion caused by a partial pressure difference at the porous partition, and the treated sample gas includes the replacement gas replacing at least part of gas components of the untreated sample gas.

As a result, unnecessary components can be removed by replacing at least part of gas components in the untreated sample gas with the replacement gas. In this case, because the flow rate of the untreated sample gas introduced into the pretreatment device and gas pressure in the pretreatment device do not fluctuate, it is not necessary to change the treatment conditions such as the flow rate and pressure of the replacement gas and it can be easily adapted to the variations in the flow rate of gas introduced into the analytical device. Furthermore, it is possible to reduce the difference in gas pressure between the regions separated by the porous partition and prevent the impediment of gas replacement via diffusion at the porous partition caused by the difference in partial pressure between the untreated sample gas and replacement gas. In addition, because gas replacement can be performed regardless of the flow rate of gas introduced into the analytical device, dissipation of fine particles or the like that are the analytical sample during gas replacement can be prevented and a constant gas replacement efficiency can be maintained.

Furthermore, when the flow rate of the untreated sample gas is changed so that the gas replacement efficiency does not change correspondingly to the type of the analytical sample, the flow rate of gas introduced into the analytical device can be maintained at a value optimum for the analysis by changing the flow rate of the carrier gas correspondingly to the variations in the flow rate of the untreated sample gas. As a result, the gas replacement efficiency in the pretreatment device can be optimized and the flow rate of gas introduced into the analytical device can be optimized, particularly in a plasma analytical device, stable plasma can be maintained.

In this case, the sample introducing system in accordance with the present invention preferably includes an introducing flow channel for introducing the untreated sample gas into the pretreatment device; wherein the pretreatment device has a first pipe and a second pipe, and the first pipe and the second pipe are separated by the porous partition; the first pipe has a first inlet port connected to the introducing flow channel, a first outlet port connected to the connection gas flow channel, and a first gas flow channel between the first inlet port and the first outlet port; the second pipe has a second inlet port connected to a supply source of a replacement gas, a second outlet port for causing a discharge gas that includes the untreated sample gas replacing the replacement gas to flow out, and a second gas flow channel between the second inlet port and the second outlet port; the diameter of pores of the porous partition is set so as to prevent substantially a gas movement via the porous partition caused by a difference between a gas pressure in the first gas flow channel and a gas pressure in the second gas flow channel; the pressure adjusting device has a branch flow channel that causes the introducing flow channel to communicate with the second outlet port in the vicinity of the first inlet port; gas suction means for sucking part of the untreated sample gas supplied to the introducing flow channel together with the discharge gas via the branch flow channel, setting means for setting an introduction flow rate of the untreated sample gas to the pretreatment device, setting means for setting a total suction flow rate of the untreated sample gas and the discharge gas sucked by the gas suction means, and setting means for setting a supply flow rate of the replacement gas to the second pipe are provided; a pressure of the untreated sample gas supplied to the introducing flow channel is set to the atmospheric pressure or a constant pressure; the introduction flow rate of the untreated sample gas is set to a constant value; a set value of the total suction flow rate of the untreated sample gas and the discharge gas is made larger than a set value of the supply flow rate of the replacement gas; and a gas discharge side of the gas suction means communicates with the ambient atmosphere or an atmosphere under a constant pressure.

As a result, the pressure of the untreated sample gas supplied to the introducing flow channel is equal to the atmospheric pressure or a constant pressure, and the set value of the total suction flow rate of the untreated sample gas and discharge gas is larger than the set value of the supply flow rate of the replacement gas to the second pipe. Therefore, part of the untreated sample gas supplied to the introducing flow channel is reliably sucked in by the gas suction means via the branch flow channel. Further, because the gas discharge side of the gas suction means communicates with an ambient atmosphere or an atmosphere under a constant pressure, the pressure of the untreated sample gas in the vicinity of the first inlet port in the introducing flow channel can be almost equal to the atmospheric pressure or a constant pressure. As a result, even when the pressure loss of the untreated sample gas is large due to a large length of the introducing flow channel and the value of pressure loss is not constant because of a difference in length and diameter of the introducing flow channel, pressure fluctuations of gas in the vicinity of the first inlet port in the introducing flow channel can be prevented, pressure fluctuations of gas in the pretreatment device can be restricted and the pretreatment device can be sealed from the ambient environment.

The analytical device is preferably a plasma analytical device having a tube for introducing the treated sample gas, to which the carrier gas has been added, into plasma.

When the addition flow rate of the carrier gas to the treated sample gas varies, since the gas is throttled in the tube, the inner pressure of the connection gas flow channel tends to change. However, because pressure fluctuations of the gas in the connection gas flow channel between the pretreatment device and the gas addition device are restricted by the pressure adjusting device, contaminating substances in the ambient environment or the like can be prevented from penetrating into the analytical device via a seal or the like of the connection portion between the pretreatment device and the connection gas flow channel, and the treated sample gas can be prevented from leaking to the outside.

The gas addition device preferably has an aspirator that introduces the treated sample gas into the connection gas flow channel based on a pressure head decrease of the carrier gas introduced into the connection gas flow channel.

As a result, the carrier gas can be added without providing a movable member or a power source in the connection gas flow channel. Further, even when the untreated sample gas itself does not have a pressure necessary to introduce the untreated sample gas into the pretreatment device, the predetermined amount of the untreated sample gas can be introduced into the pretreatment device without providing a movable member or a power source.

In accordance with the present invention, it is possible to provide a sample introducing system that has flexibility to adapt easily to a variety of analytical conditions without being affected by a flow rate of gas introduced into an analytical device, can introduce the analytical sample into the analytical device without loss, and is suitable for a simple and highly accurate high-sensitivity analysis.

BRIEF DESCRIPTION OF THE DRAWINGS

[FIG. 1] an explanatory drawing illustrating the entire configuration of the sample introducing system of the first embodiment of the present invention

[FIG. 2] an explanatory drawing of a sprayer used in the sample introducing system of the first embodiment of the present invention

[FIG. 3] a cross-sectional view for explaining the configuration of the gas addition device and pressure adjusting device in the sample introducing system of the first embodiment of the present invention

[FIG. 4] an explanatory drawing illustrating the entire configuration of the sample introducing system of the second embodiment of the present invention

[FIG. 5] a cross-sectional view for explaining the configuration of the gas addition device in the sample introducing system of the second embodiment of the present invention

[FIG. 6] a cross-sectional view for explaining the configuration of the pressure adjusting device in the sample introducing system of the second embodiment of the present invention

[FIG. 7] an explanatory drawing illustrating the entire configuration of the sample introducing system of the third embodiment of the present invention

[FIG. 8] a cross-sectional view for explaining the configuration of the gas addition device and pressure adjusting device in the sample introducing system of the third embodiment of the present invention

[FIG. 9] an explanatory drawing illustrating the entire configuration of the sample introducing system of the fourth embodiment of the present invention

[FIG. 10] a partial cross-sectional view of a pretreatment device of a modification example of the present invention

[FIG. 11] an explanatory drawing illustrating the entire configuration of the sample introducing system of a comparative example 1 . . . pretreatment device, 2 . . . inner tube, 2A . . . porous partition, 2a . . . inner inlet port, 2b . . . inner outlet port, 3 . . . outer tube, 3a . . . outer inlet port, 3b . . . outer outlet port, 8, 43, 46, 61 . . . flow rate control device, 10 . . . introducing flow channel, 20 . . . connection gas flow channel, 30 . . . analytical device, 30b . . . center tube, 40, 40A . . . gas addition device, 50, 50B, 50C . . . pressure adjusting device, 50a . . . branch flow channel, 50' . . . discharge flow channel, 50" . . . discharge flow channel outlet port, 52a . . . seal gas flow channel, 53a . . . communication flow channel, 60 . . . vacuum pump, 101, 102 . . . pipe, G1 . . . untreated sample gas, G3 . . . replacement gas, G4 . . . treated sample gas, G7 . . . carrier gas, G8 . . . seal gas, P . . . plasma

BEST MODE FOR CARRYING OUT THE INVENTION

A sample introducing system A1 of the first embodiment shown in FIG. 1 includes a pretreatment device 1 that performs a pretreatment of removing unnecessary components such as moisture, impurities, and solvent vapors from an untreated sample gas G1 including an analytical sample, and an introducing channel 10 for introducing the untreated sample gas G1 from a supply source into the pretreatment device 1.

The analytical sample that is to be pretreated may be in an liquid or gas form. For example, a sprayer 11 shown in FIG. 2 can be used as a supply source of the untreated sample gas G1. The sprayer 11 converts a solution 12 obtained by dissolving an analytical sample in a solvent into liquid droplets suspended in a spraying gas G2, removes the liquid droplets L with a large diameter, and supplies the remaining gas as a pressurized untreated sample gas G1 to the pretreatment device 1. A well-known sprayer can be used as such sprayer 11. In the present embodiment, a flow rate of the pressurized spraying gas G2 supplied from a pressure vessel such as a gas cylinder is controlled by a flow rate control device 13 such as a mass flow rate controller (MFC) or a flow rate control valve, and the flow rate control device 13 is used as setting means for setting the introduction flow rate of the untreated sample gas G1 to the pretreatment device 1.

Further, it is also possible to use a pressure vessel filled with a pressurized gas including a gaseous analytical sample as a supply source of the untreated sample gas G1, connect the pressure vessel to the pretreatment device 1 via a pipe constituting an introducing flow channel 10, and provide a flow rate control device in this pipe as setting means for setting the introduction flow rate of the untreated sample gas G1 to the pretreatment device 1.

In the present embodiment, the supply flow rate of the untreated sample gas G1 to the introducing flow channel 10 is taken as the introduction flow rate of the untreated sample gas G1 to the pretreatment device 1, and the introduction flow rate of the untreated sample gas G1 to the pretreatment device 1 is set to a constant value.

The analytical sample of the present embodiment is in the form of solid fine particles. Thus, fine particles of the analytical sample contained in the untreated sample gas G1 are made, for example, from a metal such as iron powder, a metal compound such as an oxide or a sulfide, a ceramic, or an organic substance such as polymer compound. The pretreatment device 1 includes a porous partition 2A, and has a gas replacement function of replacing at least part of gas components in the untreated sample gas G1 with a replacement gas G3 by means of diffusion caused by the partial pressure difference at the porous partition 2A. As a result, unnecessary components such as solvent vapors contained in the untreated sample gas G1 can be removed.

The pretreatment device 1 has a double-tube structure that includes an inner tube 2 as a first pipe, which is a straight tube of an annular shape in a transverse section thereof, and an outer tube 3 as a second pipe, which is a straight tube of an annular shape in a transverse section thereof and covers the inner tube 2. Both ends of the inner tube 2 protrude to the outside from the outer tube 3, and portions of the outer tube close to both ends thereof are gradually reduced in diameter and joined to the outer periphery of the inner tube 2. The shapes of the inner and outer tubes 2, 3 are not particularly limited, for example, the tubes may be straight or curved.

The inner tube 2 has an inner inlet portion 2a formed at one end as a first inlet port, an inner outlet port 2b formed at the other end as a first outlet port, and an inner gas flow channel 2c located between the inner inlet port 2a and inner outlet port 2b as a first gas flow channel. By connecting the introducing flow channel 10 to the inner inlet port 2a, the untreated sample gas G1 can be introduced into the inner gas flow channel 2c.

The outer tube 3 has an outer inlet port 3a as a second inlet port formed in a circumferential wall in the vicinity of one end to introduce the replacement gas G3, an outer outlet port 3b as a second outlet port formed in the circumferential wall in the vicinity of the other end, and an outer gas flow channel 3c as a second gas flow channel between the outer inlet port 3a and outer outlet port 3b. The outer inlet port 3a is connected to a supply source of the replacement gas G3. For example, a pressure vessel filled with a pressurized replacement gas G3 is used as the supply source, and a flow rate control device 8 such as a mass flow rate controller (MFC) or a flow rate control valve is provided in the pipe connecting the pressure vessel to the outer inlet port 3a as setting means for setting the supply flow rate of the replacement gas G3 to the outer tube 3.

The inner inlet port 2a, inner outlet port 2b, outer inlet port 3a, and outer outlet port 3b are disposed so that the flow of the untreated sample gas G1 in the inner gas flow channel 2c and the flow of the replacement gas G3 in the outer gas flow channel 3c are in the mutually opposite directions.

The inner tube 2, which is the first pipe, and the outer tube 3, which is the second pipe, are divided by the porous partition 2A. To be more precise, the section between the two ends of a circumferential wall that covers the inner gas flow channel 2c in the inner tube 2 is formed by the porous partition 2A, which serves to cause the untreated sample gas G1 to move to the outside of the inner gas flow channel 2c and also to cause the replacement gas G3 to move inside the inner gas flow channel 2c by the diffusion caused by the partial pressure difference between the untreated sample gas G1 and replacement gas G3. The diameter of pores in the porous partition 2A is set so as to prevent substantially the gas movement via the porous partition 2A caused by the difference between a gas pressure in the inner gas flow channel 2c and a gas pressure in the outer gas flow channel 3c, in the present embodiment, the diameter of pores is substantially 0.8 μm to 0.001 μm. In order to prevent the decrease in replacement efficiency of gases G1, G3 and the increase of the device in size, the diameter of pores is set to a value equal to or larger than 0.001 μm, preferably equal to or larger than 0.002 μm, more preferably equal to or larger than 0.02 μm. Further, in order to prevent the fine particles from penetrating through the pores or from being caught in the pores, and to prevent the occurrence of decreasing in the analysis accuracy and gas movement caused by the difference in gas pressure, the diameter of pores is set to a value equal to or less than 0.8 μm, preferably equal to or less than 0.5 μm, even more preferably equal to or less than 0.2 μm. The diameter of a very small number of pores, such that does not adversely affect the gas replacement function, in the porous partition 2A can be outside the range of 0.8 μm to 0.001 μm, but the range of 0.8 μm to 0.001 μm is substantially desirable. The porosity of the porous partition 2A is not particularly limited, but from the standpoint of gas replacement efficiency and mechanical strength, a range of 40% to 80% is preferred. The material of the porous partition 2A is not particularly limited provided that it is a porous material satisfying the above-described requirements, and glass such as quartz glass or ceramics is preferred, for example, Shirasu porous glass (SPG) can be used. In the sections 2B, 2C of the inner tube 2 close to both ends thereof, the inner and outer diameter are equal to those of the porous partition 2A, thereby ensuring smooth joining. The entire circumferential wall covering the inner gas flow channel 2c may be formed by the porous partition, it is sufficient to form a section covering at least part of the inner gas flow channel 2c by the porous partition 2A.

The materials of the sections 2B, 2C of the inner tube 2 close to both ends thereof and outer tube 3 are not particularly limited, and they may be formed by a plurality of different materials. For example, from the standpoint of processability, easiness of heating the untreated sample gas G1 introduced into the inner tube 2, and heat resistance, metals, ceramics, and glass are preferred, and ceramics or glass such as quartz glass is desirable.

Gas replacement with the pretreatment device 1 is performed by introducing the untreated sample gas G1 including fine particles from the inner inlet port 2a into the inner tube 2, causing this gas to flow in the inner gas flow channel 2c surrounded by the porous partition 2A, introducing the replacement gas G3 from the outer inlet port 3a into the outer tube 3, and causing this gas to flow in the direction opposite to the flow direction of the untreated sample gas G1 in the outer gas flow channel 3c around the porous partition 2A. As a result, a large portion of the untreated sample gas G1 is moved via the porous partition 2A to the outside of the inner gas flow channel 2c and part of the replacement gas G3 is moved via the porous partition 2A inside the inner gas flow channel 2c by diffusion caused by the difference in partial pressure between the untreated sample gas G1 and replacement gas G3, in other words, by using the difference in concentration between the untreated sample gas G1 inside the inner gas flow channel 2c and replacement gas G3 outside the inner gas flow channel 2c as a propulsion force. In the inner gas flow channel 2c, the concentration of untreated sample gas G1 gradually decreases and the concentration of replacement gas G3 gradually increases in the direction from the inner inlet port 2a to the inner outlet port 2b. In the outer gas flow channel 3c, the concentration of replacement gas G3 gradually decreases and the concentration of untreated sample gas G1 gradually increases in the direction from the outer inlet port 3a to the outer outlet port 3b. As a result, the replacement gas G3 that has replaced at least part of gas components of the untreated sample gas G1 constitutes a treated sample gas G4 flowing out from the inner outlet port 2b together with the fine particles and a very small amount of the untreated sample gas G1. Further, the untreated sample gas G1 and replacement gas G3 can be also caused to flow out as a discharge gas G5 from the outer outlet port 3b. In this case, the gas movement via the porous partition 2A caused by the difference in gas pressure between the inner gas flow channel 2c and outer gas flow channel 3c, that is, by the difference in gas pressure between the inside and the outside of the inner gas flow channel 2c, is substantially prevented by the porous partition 2A. Accordingly, by setting appropriately the pore diameter, porosity, thickness, tube diameter, length, and shape of the porous partition 2A, the inner diameter and shape of the outer tube 3, the flow rates of the untreated sample gas G1 and replacement gas G3, and the like, it is possible to decrease the amount of unnecessary components in the treated sample gas G4 flowing out of the inner outlet port 2b to an amount equal to or less than a critical amount that produces no adverse effect on the analysis in the analytical device.

In the pretreatment device 1, the amount of the untreated sample gas G1 moving to the outside of the inner gas flow channel 2c is almost equal to the amount of the replacement gas G3 moving into the inner gas flow channel 2c, practically all the untreated sample gas G1 in the inner gas flow channel 2c is replaced with the replacement gas G3, and fluctuations of the flow rate of the treated sample gas G4 flowing out from the inner outlet port 2b can be prevented. In this case, in the inner gas flow channel 2c, the fine particles with a diameter larger than the pore diameter of the porous partition 2A do not penetrate through the pores and are not trapped by the pores, the fine particles with a diameter equal to or less than the pore diameter have a diffusion rate lower than that of gas, and the inertia force created by the flow of diffusing gas is also very weak; therefore most of the fine particles flow out from the inner outlet port 2b together with the replacement gas G3 without moving into the outer gas flow channel 3c. As a result, the fine particles introduced together with the untreated sample gas G1 into the inner gas flow channel 2c can be supplied without loss into the analytical device together with the replacement gas G3 at a flow rate almost identical to that of the untreated sample gas G1.

The treated sample gas G4 pretreated by the pretreatment device 1 flows out from the inner inlet port 2b into the connection gas flow channel 20, and is introduced into the analytical device 30 via the connection gas flow channel 20. The analytical device 30 of the present embodiment is a plasma analytical device. The analytical device 30 has a plasma torch 30a for forming plasma P by using argon gas, nitrogen gas, helium gas or the like as a plasma gas G6, and a center tube 30b disposed in the center of the plasma torch 30a for introducing the treated sample gas G4 into the plasma P. A well-known plasma analytical device can be used. The spraying gas G2 and replacement gas G3 preferably have the same composition as the plasma gas G6.

As shown in FIG. 1 and FIG. 3, the gas addition device 40 and a pressure adjusting device 50 that is disposed downstream of the pretreatment device 1 and upstream of the gas addition device 40 are provided in the connection gas flow channel 20. The connection gas flow channel 20 passes through inside the gas addition device 40 and pressure adjusting device 50.

The gas addition device 40 adds a carrier gas G7 to the treated sample gas G4 flowing toward the analytical device 30 in the connection gas flow channel 20, and has means for changing the addition flow rate of the carrier gas G7. The gas addition device 40 of the present embodiment has an aspirator that introduces the treated sample gas G4 into the connection gas flow channel 20 based on a pressure head drop of the carrier gas G7 introduced into the connection gas flow channel 20.

To be more precise, the gas addition device 40 has a first duct 41, a second duct 42 connected to the first duct 41, and a flow rate control device 43 such as a mass flow rate controller (MFC) or a flow rate control valve as means for changing the addition flow rate of the carrier gas G7. The ducts 41 and 42 constitute part of the connection gas flow channel 20. An opening at one end of the first duct 41 constitutes a gas outflow port 20b of the connection gas flow channel 20, and is connected to an inlet port of the center tube 30b of the analytical device 30. A throttle portion 41a and a diffuser 41b connected to an outlet port of the throttle portion 41a are formed in the first duct 41. An opening at the other end of the first duct 41 is connected via the flow rate control device 43 to a supply source 44 of the carrier gas G7. An inlet port of the second duct 42 communicates with the inner outlet port 2b of the pretreatment device 1 via a first pipe 51 of an aftermentioned pressure adjusting device 50, and an outlet port of the second duct 42 communicates with an ejection region of the carrier gas G7 in the vicinity of the outlet port of the throttle portion 41a. The supply source 44 is, for example, a pressure vessel such as a gas cylinder, and supplies the pressurized carrier gas G7 to the first duct 41. As a result, the treated sample gas G4 is sucked into the connection gas flow channel 20 based on the pressure head drop caused by the ejection of the carrier gas G7, which is introduced into the connection gas flow channel 20, from the throttle portion 41a, and the carrier gas G7 is added to the treated sample gas G4. Thus, the gas addition device 40 constitutes the aspirator. A well-known one can be used as this aspirator. The addition flow rate of the carrier gas G7 is changed by the flow rate control device 43. The treated sample gas G4 to which the carrier gas G7 has been added is introduced into the plasma P via the center tube 30b of the analytical device 30. The carrier gas G7 preferably has the same composition as the plasma gas G6.

The pressure adjusting device 50 restricts pressure fluctuations of the gas including the analytical sample upstream of the gas addition device 40. The pressure adjusting device 50 of the present embodiment restricts the pressure fluctuations of the gas in the connection gas flow channel 20 between the pretreatment device 1 and the gas addition device 40. For this purpose, the pressure adjusting device 50 of the present embodiment has a first pipe 51 constituting the connection gas flow channel 20, a second pipe 52 constituting a seal gas flow channel 52a, and a joining pipe 53 that joins the first pipe 51 to the second pipe 52, and the inside of the joining pipe 53 serves as a communication flow channel 53a.

An opening at one end of the first pipe 51 constitutes a gas inflow port 20a of the connection gas flow channel 20, and is connected to the inner outlet port 2b of the pretreatment device 1. An opening at the other end of the first pipe 51 is connected to the inlet port of the second duct 42 of the gas addition device 40. As a result, the treated sample gas G4 flowing out from the pretreatment device 1 is introduced into the center tube 30b of the analytical device 30 via the connection gas flow channel 20. An inlet port 52a' of the seal gas flow channel 52a is connected to a supply source 54 of the seal gas G8 via a flow rate control device 55 such as a mass flow rate controller (MFC) or flow rate control valve, and an outlet port 52a" of the seal gas flow channel 52a communicates with the atmosphere. The outlet port 52a" of the seal gas flow channel 52a may communicate with an atmosphere under a constant pressure. A zone between the inlet port 52a' and outlet port 52a" in the seal gas flow channel 52a communicates via the communication flow channel 53a with a zone between the gas addition device 40 and pretreatment device 1 in the connection gas flow channel 20.

Where the gas pressure in the connection gas flow channel 20 upstream of the gas addition device 40 drops due, for example, to suction of the treated sample gas G4 caused by the gas addition device 40, part of the seal gas G8 introduced into the seal gas flow channel 52a from the inlet port 52a' is introduced into the connection gas flow channel 20, so that this pressure drop is canceled. As a result, the inside of the connection gas flow channel 20 is maintained under an almost atmospheric pressure between the pretreatment device 1 and the gas addition device 40. Therefore, when the addition flow rate of the carrier gas G7 changes, pressure fluctuations of gas in the pretreatment device 1 can be restricted by restricting pressure fluctuations of gas in the connection gas flow channel 20 between the pretreatment device 1 and the gas addition device 40. The seal gas G8 preferably has the same composition as the plasma gas G6. It is desirable that the flow rate of the seal gas G8 is set to a predetermined sufficient flow rate such that causes no fracture of the gas seal between the sample introducing system A1 and the outside.

With the above-described embodiment, the addition flow rate of the carrier gas G7 to the treated sample gas G4 flowing in the connection gas flow channel 20 is changed by the gas addition device 40, and pressure fluctuations of gas in the pretreatment region are restricted by the pressure adjusting device 50. As a result, the flow rate of gas introduced together with the analytical sample into the analytical device 30 can be varied without changing the flow rate of the untreated sample gas G1 introduced into the pretreatment device 1 and without generating pressure fluctuations of the gas in the pretreatment device 1. Therefore, it is not necessary to change the treatment conditions in the pretreatment device 1 and it can be adapted to a variety of analytical conditions.

Furthermore, the connection gas flow channel 20 between the pretreatment device 1 and gas addition device 40 communicates with the ambient atmosphere or an atmosphere under a constant pressure via the seal gas flow channel 52a, and the introduction flow rate of the untreated sample gas G1 introduced into the pretreatment device 1 becomes constant. As a result, when the addition flow rate of the carrier gas G7 is varied, pressure fluctuations of gas in the pretreatment device 1 can be reliably prevented without changing the flow rate of the untreated sample gas G1 introduced into the pretreatment device 1. Further, even when the addition flow rate of the carrier gas G7 changes, a uniform pressure inside the connection gas flow channel 20 between the pretreatment device 1 and the gas addition device 40 can be maintained at a constant level. Furthermore, a gas seal between the sample introducing system A1 and the outside can be provided by the seal gas G8 flowing in the seal gas flow channel 52a. Thus, pressure fluctuations in the connection gas flow channel 20 can be restricted without using a movable member, and contamination in the system can be prevented by sealing the inside of the connection gas flow channel 20 from the ambient environment. As a result, contaminating substances present in the ambient environment and the like can be prevented from penetrating into the analytical device 30 via a seal or the like at the connection portion of the pretreatment device 1 and the connection gas flow channel 20, and the treated sample gas G4 can be prevented from leaking to the outside. Therefore, stable analysis results can be obtained, particularly in a plasma analytical device 30, stable plasma P can be maintained without causing temperature variations or electron density variations in the plasma P, thereby contributing to high-sensitivity analysis.

In the pretreatment device 1, unnecessary components can be removed by replacing at least some gas components in the untreated sample gas G1 with the replacement gas G3. In this case, because the flow rate of the untreated sample gas G1 introduced into the pretreatment device 1 and gas pressure in the pretreatment device 1 do not fluctuate, it is not necessary to change the treatment conditions such as the flow rate and pressure of the replacement gas G3, and it can be easily adapted to the variations in the flow rate of gas introduced into the analytical device 30. Furthermore, it is possible to reduce the difference in gas pressure between the regions separated by the porous partition 2A and prevent the impediment of gas replacement via diffusion at the porous partition 2A caused by the difference in partial pressure between the untreated sample gas G1 and replacement gas G3. In addition, because gas replacement can be performed in the pretreatment device 1 regardless of the flow rate of gas introduced into the analytical device 30, dissipation of fine particles that are the analytical sample during gas replacement can be prevented and a constant gas replacement efficiency can be maintained. Furthermore, when the flow rate of the untreated sample gas G1 is changed so that the gas replacement efficiency does not change correspondingly to the type of the analytical sample, the flow rate of gas introduced into the analytical device 30 can be maintained at a value optimum for the analysis by changing the flow rate of the carrier gas G7 correspondingly to the variations in the flow rate of the untreated sample gas G1. As a result, the gas replacement efficiency in the pretreatment device 1 can be optimized, at the same time, the flow rate of gas introduced into the analytical device 30 can be optimized to maintain stable plasma P.

When the analytical sample is introduced into the plasma P together with a gas via the center tube 30b, the gas is throttled in the center tube 30b; therefore, if the pretreatment device 1 and analytical device 30 are directly connected, the pressure inside the connection gas flow channel 20 fluctuates due to variations in the flow rate of the gas introduced into the center tube 30b. However, in the present embodiment, the pretreatment device 1 and analytical device 30 are connected via the gas addition device 40, the flow rate of the gas introduced into the center tube 30b is changed by the gas addition device 40, and pressure fluctuations of gas in the connection gas flow channel 20 between the pretreatment device 1 and the gas addition device 40 are restricted by the pressure adjusting device 50 when the flow rate of the introduced gas is changed; therefore, contaminating substances in the ambient environment or the like can be prevented from penetrating into the system via the seal or the like of the connection portion between the pretreatment device 1 and the connection gas flow channel 20, and the treated sample gas G4 can be prevented from leaking to the outside. For example, when the inner diameter of the tip portion of the center tube 30b is 1 to 2 mm and the flow rate of gas introduced into the plasma P is 500 to 2000 ml/min, if the pretreatment device 1 and the analytical device 30 are directly connected, the pressure inside the inner tube 2 of the pretreatment device 1 becomes several hundreds Pa; therefore, the analytical sample has to be prevented from dissipating to the outside of the system via the porous partition 2A. To deal with this case, it is necessary to set strict conditions for supplying the replacement gas G3 and the like and control the gas pressure in the outer tube 3, so that it cannot be easily adapted to variations in analytical conditions in the analytical device 30. However, in the present embodiment, pressure fluctuations in the inner tube 2 can be prevented by the pressure adjusting device 50; therefore, such control of gas pressure in the inner tube 3 is unnecessary. As a consequence, the analytical conditions can be easily optimized by automatic tuning by which the flow rate of gas introduced into the plasma P is automatically switched correspondingly to the type of elements constituting the analytical sample.

By using an aspirator as the gas addition device 40, it is possible to add the carrier gas G7 without providing a movable member or a power source in the connection gas flow channel 20. Further, even when the untreated sample gas G1 itself does not have a pressure necessary to introduce the untreated sample gas into the pretreatment device 1, the predetermined amount of the untreated sample gas G1 can be introduced into the pretreatment device 1 without providing a movable member or a power source. The capability of the aspirator is not particularly limited, but it is preferred that the flow rate of the treated sample gas G4 that is sucked in is equal to or higher than the flow rate of the carrier gas G7. For example, when the flow rate of the carrier gas G7 is 500 ml/min, the flow rate of the treated sample gas G4 that is sucked in is made equal to or higher than 500 ml/min. Any material can be used to make the aspirator, provided that it causes no problems such as contamination inside the system or selective adsorption of specific components, for example, quartz glass or Tygon (trade name of Norton Performance Plastics corporation: polyvinyl chloride) can be used.

FIGS. 4 to 6 illustrate the sample introducing system A2 of the second embodiment of the present invention. In the second embodiment, components identical to those of the first embodiment are assigned with identical reference symbols and only the differences between the two embodiments are explained.

In the second embodiment, the pressure adjusting device 50 is disposed upstream of the pretreatment device 1, and the zone between the inlet port 52a' and the outlet port 52a" in the seal gas flow channel 52a is not communicate with the connection gas flow channel 20 but with the introducing flow channel 10 via the communication flow channel 53a. For this purpose, the inlet port of the second duct 42 in the gas addition device 40 of the second embodiment is directly connected to the inner outlet port 2b of the pretreatment device 1. An opening at one end of the first pipe 51 in the pressure adjusting device 50 constitutes the gas outflow port 10a of the introducing flow channel 10 and is connected to the inner inlet port 2a of the pretreatment device 1. An opening at the other end of the first pipe 51 is connected to the supply source of the untreated sample gas G1 via a pipe constituting the introducing flow channel 10. The zone between the inlet port 52a' and the outlet port 52a" in the seal gas flow channel 52a communicates via the communication flow channel 53a with the vicinity of the inner inlet port 2a of the pretreatment device 1 in the introducing flow channel 10.

Where the gas pressure in the introducing flow channel 10 drops due, e.g., to suction of the treated sample gas G4 caused by the gas addition device 40, part of the seal gas G8 introduced from the inlet port 52a' into the seal gas flow channel 52a is introduced into the introducing flow channel 10 and this pressure drop is cancelled. As a result, by restricting pressure fluctuations of gas in the introducing flow channel 10, it is possible to restrict pressure fluctuations of gas in the pretreatment device 1.

Although not only the untreated sample gas G1 but also the seal gas G8 are introduced into the pretreatment device 1 when the seal gas G8 is introduced in the introducing flow channel 10, it is not necessary to change the treatment conditions in the pretreatment device 1 because the introduction flow rate itself of the untreated sample gas G1 introduced into the pretreatment device 1 is constant.

Other aspects in this embodiment are identical to those of the first embodiment.

FIGS. 7, 8 illustrate a sample introducing system A3 of the third embodiment of the present invention. In the third embodiment, components identical to those of the first embodiment are assigned with identical reference symbols and only the differences between the two embodiments are explained.

In the third embodiment, the pressure adjusting device 50B is disposed upstream of the pretreatment device 1, and prevents gas pressure fluctuations without using the seal gas. For this purpose, the pressure adjusting device 50B of the third embodiment has a discharge flow channel 50' that branches off from the introducing flow channel 10 instead of the configuration of the pressure adjusting device 50 in the first embodiment. In the present embodiment, because the discharge flow channel 50' branches off from the introducing flow channel 10, the discharge flow channel 50' and introducing flow channel 10 are formed by a T-shaped pipe. Part of the pressurized untreated sample gas G1 supplied to the introducing flow channel 10 in the same manner as in the first embodiment is introduced into the pretreatment device 1, and the remaining untreated sample gas is discharged from an outlet port 50" of the discharge flow channel 50'. The outlet port 50" of the discharge flow channel 50' communicates with the ambient atmosphere. The outlet port 50" of the discharge flow channel 50' may communicate with an atmosphere under a constant pressure.

The inlet port of the second duct 42 in the gas addition device 40A of the third embodiment is directly connected to the inner outlet port 2b of the pretreatment device 1. Further, the gas addition device 40A of the third embodiment has a third duct 45 and a flow rate control device 46 in addition to the configuration identical to the gas addition device 40 of the first embodiment. An opening at one end of the third duct 45 is connected to the inside of the first duct 41 downstream of the diffuser 41b, and an opening at the other end of the third duct 45 is connected to a supply source 47 of a carrier gas G7' via the flow rate control device 46. The supply source 47 can be, for example, a pressure vessel such as a gas cylinder, and it supplies the pressurized carrier gas G7' via the third duct 45 to the first duct 41. The carrier gas G7' preferably has the same composition as the plasma gas G6. As a result, in the gas addition device 40A of the third embodiment, not only the carrier gas G7 supplied from the supply source 44 via the flow rate control device 43 but also the carrier gas G7' supplied from the supply source 47 via the flow rate control device 46 are added to the treated sample gas G4. Means for changing the addition flow rate of the carrier gas G7' added by the gas addition device 40A in the third embodiment is constituted by the flow rate control device 46.

In the third embodiment, the suction flow rate of the untreated sample gas G1 sucked by the aspirator constituted by the gas addition device 40A is taken as the introduction flow rate of the untreated sample gas G1 to the pretreatment device 1. Because this suction flow rate is determined correspondingly to the flow rate of the carrier gas G7 that is set by the flow rate control device 43, the flow rate control device 43 functions as means for setting the introduction flow rate of the untreated sample gas G1 to the pretreatment device 1. The introduction flow rate of the untreated sample gas G1 to the pretreatment device 1 is set to a constant value.

In the third embodiment, the pressurized untreated sample gas G1 is supplied to the introducing flow channel 10 in the same manner as in the first embodiment, and means for setting the supply flow rate of the untreated sample gas G1 to the introducing flow channel 10 is provided. When the untreated sample gas G1 is supplied to the introducing flow channel 10 with the sprayer 11 in the same manner as in the first embodiment, the flow rate control device 13 that sets the flow rate of the spraying gas G2 functions as means for setting the supply flow rate of the untreated sample gas G1. Further, it is also possible to use a pressure vessel serving as the supply source filled with a pressurized gas including a gaseous analytical sample as the untreated sample gas G1, and connect the pressure vessel to the introducing flow channel 10 via the flow rate control device that functions as means for setting the supply flow rate. The set value of the supply flow rate of the untreated sample gas G1 to the introducing flow channel 10 is larger than the set value of the introduction flow rate of the untreated sample gas G1 to the pretreatment device 1.

Other aspects in this embodiment are identical to those of the first embodiment.

With the third embodiment, the outlet port of the discharge flow channel 50' communicates with the ambient atmosphere or an atmosphere under a constant pressure, and the introduction flow rate of the untreated sample gas G1 introduced into the pretreatment device 1 is constant, therefore pressure fluctuations of gas in the pretreatment device 1 can be reliably prevented without changing the flow rate of the untreated sample gas G1 introduced into the pretreatment device 1. Further, because the set value of the supply flow rate of the untreated sample gas G1 to the introducing flow channel 10 is larger than the set value of the introduction flow rate of the untreated sample gas G1 to the pretreatment device 1, a gas seal between the sample introducing system A3 and the outside can be ensured by the untreated sample gas G1 flowing in the discharge flow channel 50'. Thus, pressure fluctuations of gas in the pretreatment device 1 can be restricted and sealing from the ambient environment can be provided without using a movable member.

FIG. 9 illustrates a sample introducing system A4 of the fourth embodiment of the present invention. In the fourth embodiment, components identical to those of the first embodiment are assigned with identical reference symbols and only the differences between the two embodiments are explained.

In the fourth embodiment, the pressure of the untreated sample gas G1 supplied to the introducing flow channel 10 is the atmospheric pressure or a constant pressure, and the inlet port of the introducing flow channel 10 directly communicates with the atmosphere of the untreated sample gas G1 without any flow rate control device such as a mass flow rate controller (MFC) or a flow rate control valve. For example, the inlet port of the introducing flow channel 10 communicates with the ambient atmosphere or an atmosphere under a constant pressure, and the ambient atmosphere or the atmosphere under a constant pressure is taken as the untreated sample gas G1.

In the fourth embodiment, the pressure adjusting device 50C is disposed upstream of the pretreatment device 1, and pressure fluctuations of gas are prevented without using a seal gas. The pressure adjusting device 50C of the fourth embodiment has a branch flow channel 50a that branches off from the introducing flow channel 10 instead of the configuration of the pressure adjusting device 50 in the first embodiment. One end of a pipe constituting the branch flow channel 50a is connected to a pipe constituting the introducing flow channel 10 in the vicinity of the inner inlet port 2a of the pretreatment device 1, and the other end of the pipe constituting the branch flow channel 50a is connected to the outer outlet port 3b of the pretreatment device 1. As a result, the branch flow channel 50a causes the introducing flow channel 10 to communicate with the outer outlet port 3b in the vicinity of the inner inlet port 2a.

Gas suction means is provided for sucking part of the untreated sample gas G1 supplied to the introducing flow channel 10 together with the discharge gas G5 from the outer outlet port 3b of the pretreatment device 1 via the branch flow channel 50a. The gas suction means of the present embodiment is constituted by a vacuum pump 60, and a gas suction side of the vacuum pump 60 is connected via a flow rate control device 61 to the pipe constituting the branch flow channel 50a. A gas discharge side of the vacuum pump 60 communicates with the ambient atmosphere. The gas suction means is not limited to the vacuum pump 60 and may be constituted, for example, by a blower or a fan. Further, the gas discharge side of the vacuum pump 60 may communicate with an atmosphere under a constant pressure. The flow rate control device 61 constitutes means for setting a total suction flow rate of the untreated sample gas G1 and discharge gas G5 that are sucked by the vacuum pump 60. A set value of the total suction flow rate of the untreated sample gas G1 and discharge gas G5 that are sucked by the vacuum pump 60 is larger than a set value of the supply flow rate of the replacement gas G3 to the outer tube 3 that is set by the flow rate control device 8.

In the fourth embodiment, the gas addition device 40A identical to that of the third embodiment is provided instead of the gas addition device 40 of the first embodiment, and the flow rate control device 46 acts as means for changing the addition flow rate of the carrier gas G7' added by the gas addition device 40A. Further, in the fourth embodiment, the suction flow rate of the untreated sample gas G1 sucked by the aspirator constituted by the gas addition device 40A is taken as the introduction flow rate of the untreated sample gas G1 to the pretreatment device 1. This suction flow rate is determined according to the flow rate of the carrier gas G7 set by the flow rate control device 43, therefore the flow rate control device 43 functions as means for setting the introduction flow rate of the untreated sample gas G1 to the pretreatment device 1. The introduction flow rate of the untreated sample gas G1 to the pretreatment device 1 is set to a constant value.

Other aspects in this embodiment are identical to those of the first embodiment.

With the fourth embodiment, the pressure of the untreated sample gas G1 supplied to the introducing flow channel 10 is equal to the atmospheric pressure or a constant pressure, and the set value of the total suction flow rate of the untreated sample gas G1 and discharge gas G5 is larger than the set value of the supply flow rate of the replacement gas G3 to the outer tube 3. As a result, part of the untreated sample gas G1 supplied to the introducing flow channel 10 is reliably sucked by the vacuum pump 60 via the branch flow channel 50a. Further, the gas discharge side of the vacuum pump 60 communicates with the ambient atmosphere or an atmosphere under a constant pressure, therefore the pressure of the untreated sample gas G1 in the vicinity of the inner inlet port 2a in the introducing flow channel 10 can be almost equal to the atmospheric pressure or a constant pressure. As a result, even when the pressure loss of the untreated sample gas G1 is large due to a large length of the introducing flow channel 10 and the value of pressure loss is not constant because of a difference in length or diameter of the introducing flow channel 10, pressure fluctuations of gas in the vicinity of the inner inlet port 2a in the introducing flow channel 10 can be prevented, and pressure fluctuations of gas in the pretreatment device 1 can be restricted and the pretreatment device 1 can be sealed from the ambient environment.

The present invention is not limited to the above-described embodiment.

For example, the pressure adjusting device may be configured by a pressure adjusting valve.

Further, in the first and second embodiments, the gas addition device may have constitution in which the treated sample gas is sucked by gas suction means such as a pump, a blower, or a fan instead of the aspirator, and the carrier gas discharged from a high-pressure cylinder or pump via a flow rate control device such as a mass flow rate controller (MFC) or a flow rate control valve is added to the treated sample gas in a connection gas flow channel downstream of the gas suction means.

In the third and fourth embodiments, the carrier gas G7' can be added to the treated sample gas G4 from the supply source 47 via the flow rate control device 46, therefore the gas addition device 40A may have gas suction means such as a pump, a blower, or a fan that sucks the untreated sample gas G1 instead of the aspirator.

Further, in the pretreatment device 1 of the above-described embodiment, the inner tube 2 serves as a first pipe and the outer tube 3 serves as a second pipe, but the inner tube 2 may serve as the second pipe and the outer tube 3 may serve as the first pipe. In this case, the inner inlet port 2a serves as the second inlet port, the inner outlet port 2b serves as the second outlet port, the inner gas flow channel 2c serves as the second gas flow channel, the outer inlet port 3a serves as the first inlet port, the outer outlet port 3b serves as the first outlet port, and the outer gas flow channel 3c serves as the first gas flow channel. As a result, the inner inlet port 2a is connected to the supply source of the replacement gas G3, the untreated sample gas G1 and replacement gas G3 flow out as the discharge gas G5 from the inner outlet port 2b, the untreated sample gas G1 is introduced into the outer gas flow channel 3c by connecting the introducing flow channel 10 to the outer inlet port 3a, and the treated sample gas G4 is introduced into the analytical device 30 via the connection gas flow channel 20 connected to the outer outlet port 3b.

Further, the pretreatment device 1 of the above-described embodiments has a double-tube structure in which the inner tube 2 serves as the first pipe and the outer tube 3 serves as the second pipe, but instead of this structure, a modification example shown in FIG. 10 may be employed, in which two pipes 101, 102 disposed parallel to each other are provided, and the two pipes 101, 102 share the porous partition 2A. In this case, one of the two pipes 101, 102 serves as the first pipe, the other serves as the second pipe, and the two pipes 101, 102 are separated by the porous partition 2A.

The analytical device is not limited to the plasma analytical device, for example, an analytical device that performs analysis by a gas chromatography mass spectrometry may be employed.

A method for removing the unnecessary components with the pretreatment device is not limited to the above-described embodiments, for example, it is possible to use a drier that removes moisture as an unnecessary component, or a fine particle classification device in which gaseous contaminating components are removed when fine particles serving as an analytical sample are electrically charged and classified, and the fine particles are suspended in an atmosphere composed of desired gas species, as described in the section of the description relating to prior art.

EXAMPLE 1

The sample introducing system A1 of the first embodiment was used, the flow rate of gas introduced into the center tube 30b of the analytical device 30 was changed, and the gas flow rate in the center tube 30b and gas pressure in the inner outlet port 2b of the pretreatment device 1 were measured.

In the present example, the flow rate of the untreated sample gas G1 was constant (300 ml/min), and the flow rate of gas introduced into the center tube 30b of the analytical device 30 was changed by changing the flow rate of the carrier gas G7.

The inner diameter of the tip portion of the center tube 30b of the analytical device 30 was 1.5 mm. The gas pressure in the outer outlet port 3b of the pretreatment device, 1, outlet port 52*a*" of the sealed gas flow channel 52*a*, and outlet port of the center tube 30*b* was atmospheric pressure.

EXAMPLE 2

The gas pressure in the inner outlet port 2*b* of the pretreatment device 1 was measured in the same manner as in Example 1, except that the inner diameter of the tip portion of the center tube 30*b* was 1.8 mm.

COMPARATIVE EXAMPLE 1

A sample introducing system B of a comparative example shown in FIG. 11 was used instead of the sample introducing system A1 of the first embodiment, the flow rate of gas introduced into the center tube 30*b* of the analytical device 30 was changed, and the gas pressure in the inner outlet port 2*b* of the pretreatment device 1 was measured.

The sample introducing system B of the comparative example had a configuration identical to that of the sample introducing system A1 of the embodiment, except that the gas addition device 40 and pressure adjusting device 50 were removed and the pretreatment device 1 and analytical device 30 were directly connected via the connection gas flow channel 20; components identical to those of the sample introducing system A1 of the embodiment are assigned with identical symbols.

In the sample introducing system B of the comparative example, the flow rate of the untreated sample gas G1 was changed in the same manner as the flow rate of gas introduced into the center tube 30*b* of the analytical device 30 in Example 1.

The inner diameter of the tip portion of the center tube 30*b* of the analytical device 30 was 1.5 mm. The gas pressure in the outer outlet port 3*b* of the pretreatment device 1 and the outlet port of the center tube 30*b* was atmospheric pressure.

COMPARATIVE EXAMPLE 2

The gas pressure in the inner outlet port 2*b* of the pretreatment device 1 was measured in the same manner as in Comparative Example 1, except that the inner diameter of the tip portion of the center tube 30*b* was 1.8 mm.

The measurement results obtained in the examples are shown in Table 1 below. The measurement results obtained in the comparative examples are shown in Table 2.

It can be confirmed from Table 1 and Table 2 that in Examples 1 and 2, the gas pressure in the inner outlet port 2*b* of the pretreatment device 1 is almost equal to the atmospheric pressure, the gas pressure is almost constant due to the action of the pressure adjusting device 50 regardless of the difference in the diameter of the center tube 30*b*, and large gas pressure fluctuations observed in Comparative Examples 1 and 2 do not occur. Thus, the examples of the present invention confirm that even when the flow rate of the carrier gas G7 changes in response to changes in the analytical conditions in the analytical device 30, dissipation of fine particles or the like that are an analytical sample can be prevented and the gas replacement efficiency in the pretreatment device 1 can be maintained at a constant level.

The invention claimed is:

1. A sample introducing system comprising:
   a pretreatment device that performs a pretreatment of removing unnecessary components from an untreated sample gas containing an analytical sample;
   a connection gas flow channel that introduces a treated sample gas treated by said pretreatment device into an analytical device;
   a gas addition device that adds a carrier gas to said treated sample gas that flows toward said analytical device in said connection gas flow channel; and
   a pressure adjusting device that restricts pressure fluctuations of a gas including said analytical sample upstream of said gas addition device, wherein
   said gas addition device comprises changing means for changing an addition flow rate of said carrier gas.

2. The sample introducing system according to claim 1, wherein said pressure adjusting device has a seal gas flow channel and a communication flow channel;
   said seal gas flow channel has an inlet port connected to a supply source of a seal gas and an outlet port communicating with an ambient atmosphere or an atmosphere under a constant pressure;
   a zone between said inlet port and said outlet port of said seal gas flow channel communicates via said communication flow channel with a zone between said gas addition device and said pretreatment device in said connection gas flow channel;
   setting means for setting an introduction flow rate of said untreated sample gas to said pretreatment device is provided; and

TABLE 1

| | | | | | | | | |
|---|---|---|---|---|---|---|---|---|
| Flow rate of untreated sample gas (ml/min) | | 300 | 300 | 300 | 300 | 300 | 300 | 300 |
| Flow rate of carrier gas (ml/min) | | 450 | 500 | 550 | 600 | 650 | 700 | 750 |
| Flow rate of gas in center tube (ml/min) | | 770 | 876 | 985 | 1098 | 1213 | 1328 | 1444 |
| Pressure in inner outlet port (Pa) | Example 1 | 3 | 3 | 3 | 3 | 2 | 2 | 2 |
| | Example 2 | 3 | 3 | 3 | 2 | 2 | 2 | 2 |

TABLE 2

| | | | | | | | | |
|---|---|---|---|---|---|---|---|---|
| Flow rate of untreated sample gas (ml/min) | | 770 | 876 | 985 | 1098 | 1213 | 1328 | 1444 |
| Pressure in inner outlet port (Pa) | Comparative Example 1 | 104 | 127 | 160 | 201 | 244 | 288 | 328 |
| | Comparative Example 2 | 91 | 107 | 132 | 165 | 196 | 227 | 257 | the introduction flow rate of said untreated sample gas is set to a constant value.

3. The sample introducing system according to claim 1, comprising an introducing flow channel for introducing said untreated sample gas into said pretreatment device; wherein
said pressure adjusting device has a seal gas flow channel and a communication flow channel;
said seal gas flow channel has an inlet port connected to a supply source of a seal gas and an outlet port communicating with an ambient atmosphere or an atmosphere under a constant pressure;
a zone between said inlet port and said outlet port of said seal gas flow channel communicates via said communication flow channel with said introducing flow channel;
setting means for setting an introduction flow rate of said untreated sample gas to said pretreatment device is provided; and
said introduction flow rate of said untreated sample gas is set to a constant value.

4. The sample introducing system according to claim 1, comprising an introducing flow channel for introducing said untreated sample gas into said pretreatment device; wherein
said pressure adjusting device has a discharge flow channel that branches off from said introducing flow channel;
said discharge flow channel has an outlet port communicating with an ambient atmosphere or an atmosphere under a constant pressure;
setting means for setting a supply flow rate of said untreated sample gas to said introducing flow channel, and setting means for setting an introduction flow rate of said untreated sample gas to said pretreatment device are provided;
said introduction flow rate of said untreated sample gas is set to a constant value; and
a set value of said supply flow rate of said untreated sample gas is larger than a set value of said introduction flow rate.

5. The sample introducing system according to claim 1, comprising
an introducing flow channel for introducing the untreated sample gas into said pretreatment device; wherein
said analytical sample is in the form of solid fine particles;
said pretreatment device has a first pipe, a second pipe, and a porous partition that separates said first pipe from said second pipe;
said first pipe has a first inlet port connected to said introducing flow channel, a first outlet port connected to said connection gas flow channel, and a first gas flow channel between said first inlet port and said first outlet port;
said second pipe has a second inlet port connected to a supply source of a replacement gas, a second outlet port for causing a discharge gas that includes said untreated sample gas replacing said replacement gas to flow out, and a second gas flow channel between said second inlet port and said second outlet port;
a gas replacement function is realized with said pretreatment device by which at least part of gas components of said untreated sample gas are replaced with said replacement gas via diffusion caused by a partial pressure difference at said porous partition, and said treated sample gas includes said replacement gas replacing at least part of gas components of said untreated sample gas;
the diameter of pores of said porous partition is set so as to prevent substantially a gas movement via said porous partition caused by a difference between a gas pressure in said first gas flow channel and a gas pressure in said second gas flow channel;
said pressure adjusting device has a branch flow channel that causes said introducing flow channel to communicate with said second outlet port in the vicinity of said first inlet port;
gas suction means for sucking part of said untreated sample gas supplied to said introducing flow channel together with said discharge gas via said branch flow channel, setting means for setting an introduction flow rate of said untreated sample gas to said pretreatment device, setting means for setting a total suction flow rate of said untreated sample gas and said discharge gas sucked by said gas suction means, and setting means for setting a supply flow rate of said replacement gas to said second pipe are provided;
a pressure of said untreated sample gas supplied to said introducing flow channel is set to the atmospheric pressure or a constant pressure;
the introduction flow rate of the untreated sample gas is set to a constant value;
a set value of the total suction flow rate of said untreated sample gas and said discharge gas is made larger than a set value of said supply flow rate of said replacement gas; and
a gas discharge side of said gas suction means communicates with the ambient atmosphere or an atmosphere under a constant pressure.

6. The sample introducing system according to any of claims 1 to 4, wherein
said analytical sample is in the form of solid fine particles;
said pretreatment device has a porous partition; and
a gas replacement function is realized with said pretreatment device by which at least part of gas components of said untreated sample gas are replaced with said replacement gas via diffusion caused by a partial pressure difference at said porous partition, and said treated sample gas includes said replacement gas replacing at least part of gas components of said untreated sample gas.

7. The sample introducing system according to any one of claims 1 to 4, wherein said analytical device is a plasma analytical device having a tube for introducing said treated sample gas, to which said carrier gas is added, into plasma.

8. The sample introducing system according to any one of claims 1 to 4, wherein said gas addition device has an aspirator that introduces said treated sample gas into said connection gas flow channel based on a pressure head decrease of the carrier gas introduced into said connection gas flow channel.

* * * * *